United States Patent
Foucher et al.

(10) Patent No.: US 10,661,018 B2
(45) Date of Patent: *May 26, 2020

(54) DRUG CONTAINER

(71) Applicant: Fresenius Kabi Deutschland GmbH, Bad Homburg (DE)

(72) Inventors: Cedric Foucher, Grenoble (FR); Lionel Lefebvre, Seyssins (FR); Michel Vernizeau, Valence (FR)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 236 days.

This patent is subject to a terminal disclaimer.

(21) Appl. No.: 15/670,178

(22) Filed: Aug. 7, 2017

(65) Prior Publication Data
US 2017/0333634 A1 Nov. 23, 2017

Related U.S. Application Data

(63) Continuation of application No. 13/132,285, filed as application No. PCT/IB2008/003736 on Dec. 2, 2008, now Pat. No. 9,731,082.

(51) Int. Cl.
*A61M 5/31* (2006.01)
*A61M 5/34* (2006.01)
(Continued)

(52) U.S. Cl.
CPC .............. *A61M 5/3134* (2013.01); *A61J 1/20* (2013.01); *A61M 5/344* (2013.01); *A61M 5/347* (2013.01); *A61J 1/00* (2013.01); *A61M 5/00* (2013.01)

(58) Field of Classification Search
CPC ..... A61J 1/2096; A61J 1/2089; A61B 19/026; A61M 5/344; A61M 5/3134; B65B 55/00
See application file for complete search history.

(56) References Cited

U.S. PATENT DOCUMENTS 3,770,155 A 11/1973 Novitch
3,987,930 A * 10/1976 Fuson .................. A61M 39/20
220/287
(Continued)

FOREIGN PATENT DOCUMENTS

EP 0 882 441 A2 12/1998
EP 1 557 367 A1 7/2005
(Continued)

OTHER PUBLICATIONS

European Patent Office, International Search Report in International Application No. PCT/IB2008/003736 (dated Jun. 4, 2009).
(Continued)

*Primary Examiner* — Bradley J Osinski
(74) *Attorney, Agent, or Firm* — Leydig, Voit & Mayer, Ltd.

(57) ABSTRACT

The present invention relates to an assembly (101) comprising: an injection device (1) comprising a container (2) for a product, said container comprising a distal tip (3), an adaptor (5) comprising a ring (6) mounted onto said distal tip (3), characterized in that said assembly (101) further comprises a heat-shrinkable film (9) covering part (2a) of said container (2) and part (5a) of said adaptor (5), said film (9) maintaining said adaptor (5) blocked in rotation and in translation with respect to said container (2) when said film (9) is in its heat-shrunk condition. The invention further relates to a method for manufacturing such an assembly.

16 Claims, 5 Drawing Sheets

Figure 1:
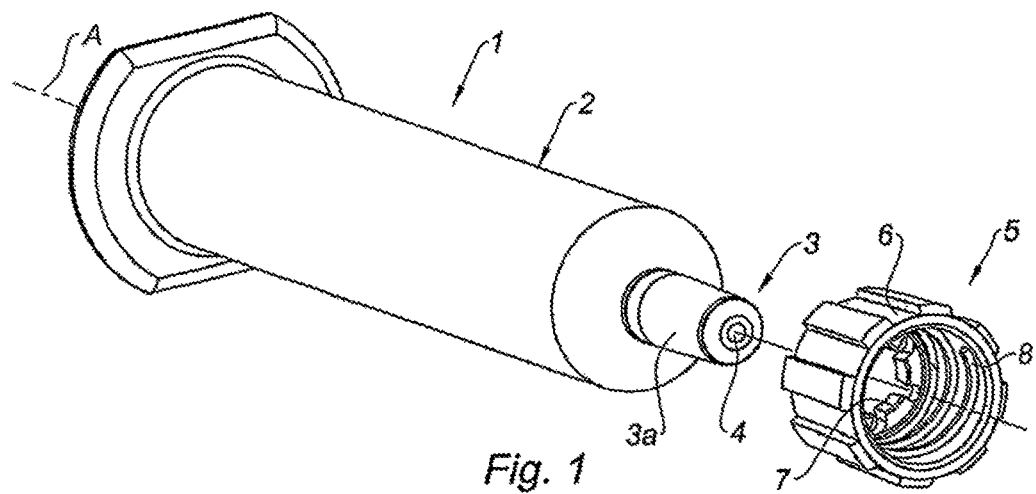

(51) Int. Cl.
    *A61J 1/20*     (2006.01)
    *A61J 1/00*     (2006.01)
    *A61M 5/00*     (2006.01)

(56) References Cited

U.S. PATENT DOCUMENTS

| | | |
|---|---|---|
| 5,154,725 A | 10/1992 | Leopold |
| 5,171,214 A | 12/1992 | Kolber et al. |
| 5,605,230 A | 2/1997 | Marino, Jr. et al. |
| 6,105,777 A | 8/2000 | Castellarin et al. |
| 2006/0010651 A1 | 1/2006 | Honda et al. |
| 2006/0108319 A1 | 5/2006 | Meittunen |

FOREIGN PATENT DOCUMENTS

| | | |
|---|---|---|
| JP | 2007-061476 A | 3/2007 |
| JP | 2008-035913 A | 2/2008 |
| WO | WO 1998/026819 A1 | 6/1998 |

OTHER PUBLICATIONS

European Patent Office, Written Opinion in International Application No. PCT/IB2008/003736 (dated Jun. 4, 2009).

International Bureau of WIPO, International Preliminary Report on Patentability in International Application No. PCT/IB2008/003736 (dated Jun. 7, 2011).

\* cited by examiner

# DRUG CONTAINER

CROSS-REFERENCE TO RELATED APPLICATIONS

This patent application is a continuation of co-pending U.S. patent application Ser. No. 13/132,285, filed Oct. 17, 2011, which is the U.S. national phase of International Application No. PCT/IB2008/003736, filed on Dec. 2, 2008, the disclosures of which are incorporated herein by reference in their entireties for all purposes.

BACKGROUND OF THE INVENTION

The present invention relates to an assembly comprising an injection device having a distal tip on which is mounted an adaptor element, such as a Luer lock adaptor, further comprising a means for preventing the rotation of the adaptor with respect to the distal tip.

In this application, the distal end of a component or of a device is to be understood as meaning the end furthest from the user's hand and the proximal end is to be understood as meaning the end closest lo the user's hand. Likewise, in this application, the "distal direction" is to be understood as meaning the direction of injection, and the "proximal direction" is to be understood as meaning the opposite direction to the direction of injection.

Various medical devices are known for transferring and/or storing medical fluids, such as syringes, perfusion and transfusion devices and connectors. It is essential that these various medical devices can he assembled together correctly and securely.

A conventional injection device usually comprises a hollow body forming a container for a medical product: the distal end of the body forming the container usually comprises a tip in which an axial passageway is arranged through which the said product is ejected from the container.

The handling of liquid products, in particular for a parenteral administration to a patient which is carried out via a perfusion device, as often in hospitals or in emergency situations, implies, in a general manner, the use of connectors. Such connectors make it possible to seal assemblies of medical devices and provide protection against the contamination of the medical liquid products that they contain.

The connectors, like for example IV (Intra Venous) connectors, are usually connected to the injection device by means of intermediate elements such as adaptors. Usually, these adaptors are first mounted by friction on the distal tip of the injection device: the connector, such as an IV connector, is then mounted on the free end of the adaptor, for example by screwing. In such a step, the adaptors are friction fitted on the distal tip and are supposed to remain immobile, thanks to the friction forces, with respect to the distal tip while the connector is screwed on the adaptor. However, problems have been reported concerning the use of some adaptors with various injection devices: for example, the adaptors do not remain immobile with respect to the distal tip. In particular, the friction forces are not important enough to prevent the adaptor from rotating with respect to the distal tip. It is therefore difficult for the user to determine whether the connector is well fitted in the adaptor or not and, as a consequence, whether the connector is well connected to the distal tip of the injection device. An incorrect connection between the injection device and the connector may cause leaks of product and therefore incorrect doses administered to the patient.

There is therefore a need for an injection device that would allow the reproducible connection between said injection device and an adaptor, so that the user knows when the connector is correctly connected to the injection device via the adaptor.

One aspect of the present invention is an assembly comprising:

an injection device comprising a container for a product, said container comprising a distal tip encompassing a channel providing a passageway for the transfer of said product, an adaptor comprising a ring mounted onto said distal tip, characterized in that said assembly further comprises a heat-shrinkable film covering at least part of said container and at least part of said adaptor, said heat-shrinkable film maintaining said adaptor blocked in rotation and in translation with respect to said container when said heat-shrinkable film is in its heal-shrunk condition.

Because at least part of the adaptor is imprisoned within the shrink film together with at least part of the container, the adaptor is firmly fixed with respect to said container, and therefore to said distal tip and it is prevented from rotating and translating with respect to the distal tip of the injection device. The user can simply screw the connector to the adaptor by grasping in his fingers the assembly via the shrunk film on one hand, and the connector on the other hand. Since the adaptor is not allowed to move with respect to the distal tip of the container, the user is certain to correctly screw the connector to the adaptor and then to the injection device.

In an embodiment of the invention, the ring of the adaptor is mounted on said distal tip by friction.

Preferably, the heat-shrinkable film covers part of said container and part of said adaptor in a continuous way.

In an embodiment of the invention, said heat-shrinkable film is made of a thermoplastic material selected from the group consisting of polyvinyl chloride (PVC), polyethylene terephthalate (PET), oriented polystyrene (OPS), oriented polypropylene \OPP), polylactic acid (PLA) and mixtures thereof. In an embodiment of the invention, the heat-shrinkable film is made of polyvinyl chloride.

The assembly of the invention may further comprise a label imprisoned between said heat-shrinkable film and said container and/or adaptor. In another embodiment of the invention, the assembly comprises a label located on said heat-shrinkable film. Said label may be made of paper and may be printed, for example with information relating to the contents of the container.

In an embodiment of the invention, the assembly further comprises a plug mounted on said adaptor. The plug is removably mounted on the adaptor, for example by friction or by screwing, and it is intended to close access to the adaptor. The heat-shrinkable film may also cover at least part of said plug. In such a case, for example, said heat-shrinkable film is provided with an annular breakable line located on the part of the heat-shrinkable film that covers part of said plug. The annular breakable line needs be broken in order to remove the plug and open the adaptor. The annular breakable line therefore constitutes a tamper evident means of the opening of the adaptor.

In another embodiment of the invention, said heat-shrinkable film is at least partially glued on at least one of said container or adaptor.

The heat-shrinkable film may also be provided with writing.

Another aspect of the invention is a method for manufacturing an assembly as defined above comprising the following steps:

a°) an injection device comprising a container for a product, said container comprising a distal tip encompassing a channel providing a passageway for the transfer of said product, and a suitable adaptor are provided, b°) the suitable adaptor is fitted on the distal tip of said injection device, c°) a heat-shrinkable film, for example under the form of a rectangular sheet, is bonded on the assembly so as to cover at least part of the adaptor and at least part of said container, d°) the heat-shrinkable film is heated until it shrinks and tightly covers said part of said container and said part of said adaptor so as to maintain said adaptor blocked in rotation and in translation with respect to said container.

In an embodiment of the invention, a plug is further provided in step a°) and mounted on the adaptor, and the heat-shrinkable film is chosen in step c°) so as to further cover at least part of said plug. In an embodiment, before the bonding step of c°), a breakable line, for example under the form of a dot-line, may be designed on the part of the heat-shrinkable film intended to cover part of said plug.

BRIEF SUMMARY OF THE INVENTION

Brief Description of the Several Views of the Drawing(s)

Figure 2:
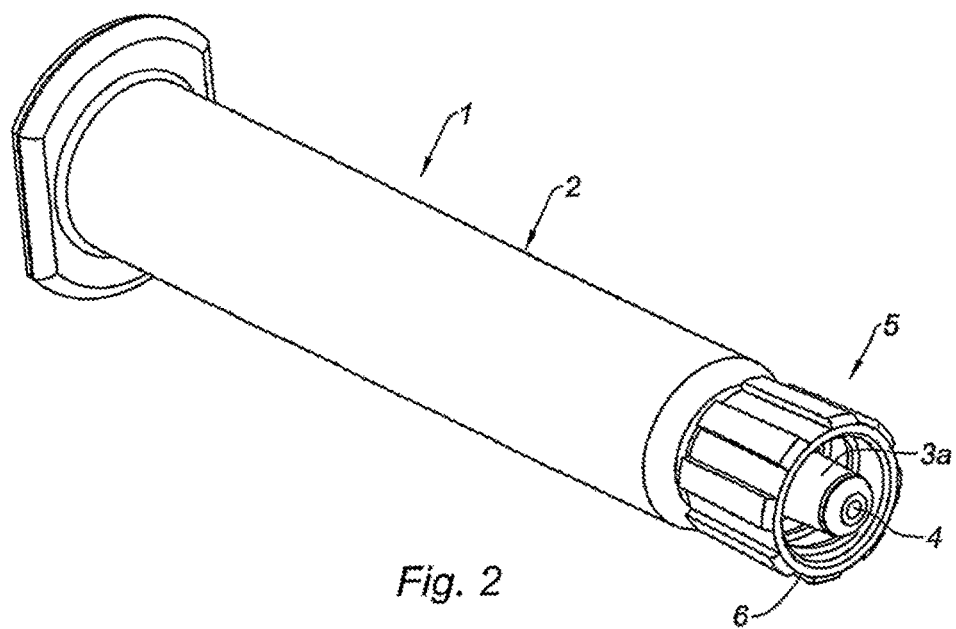
Figure 3:
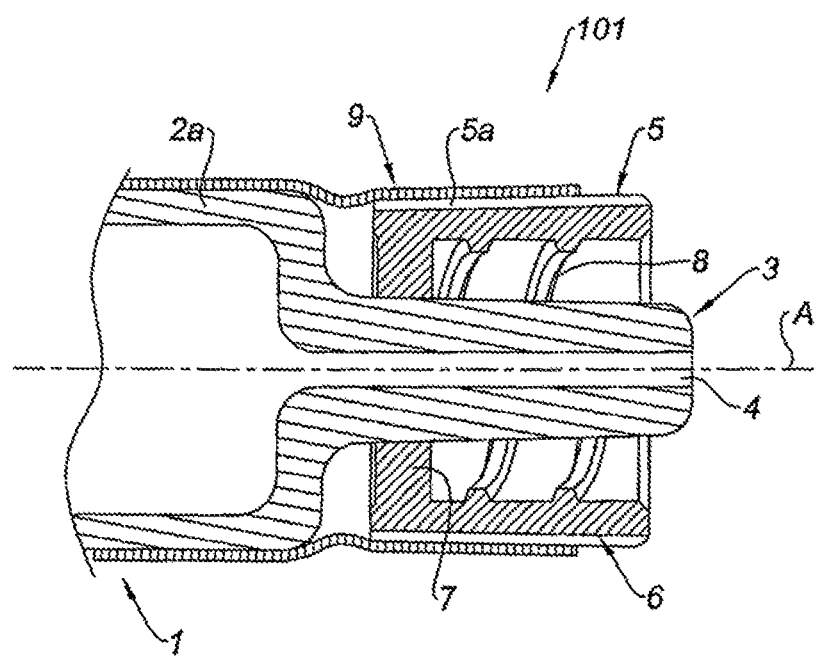
Figure 4:
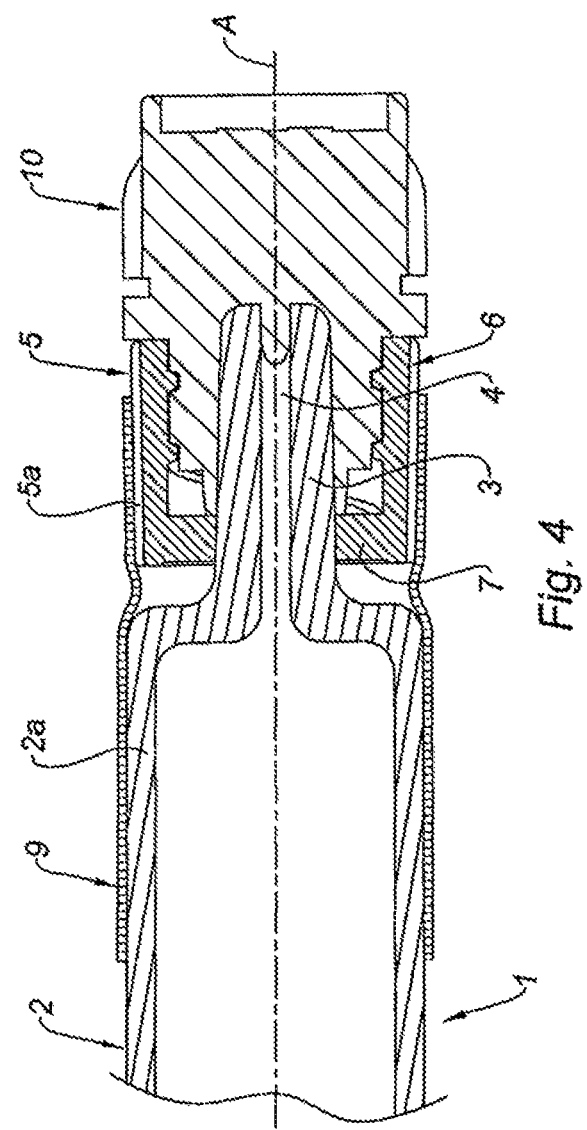
Figure 5:
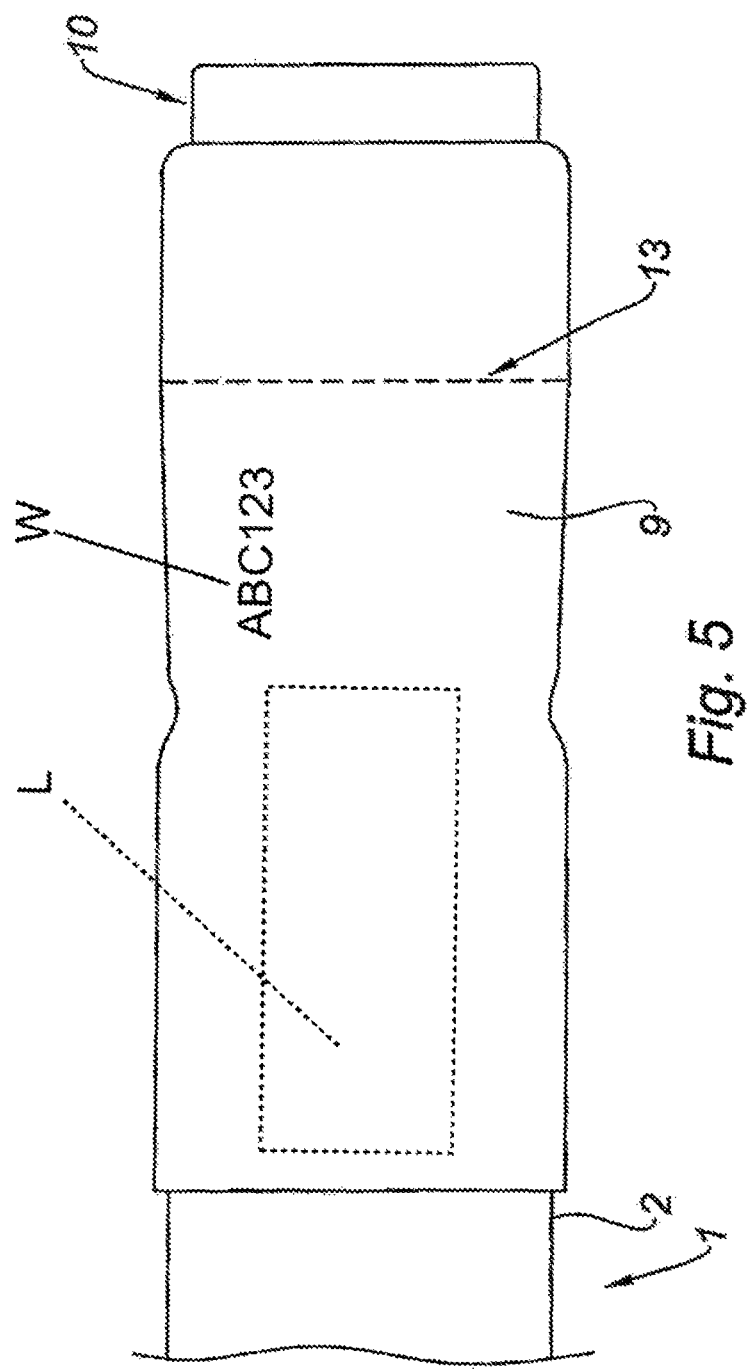
Figure 6:
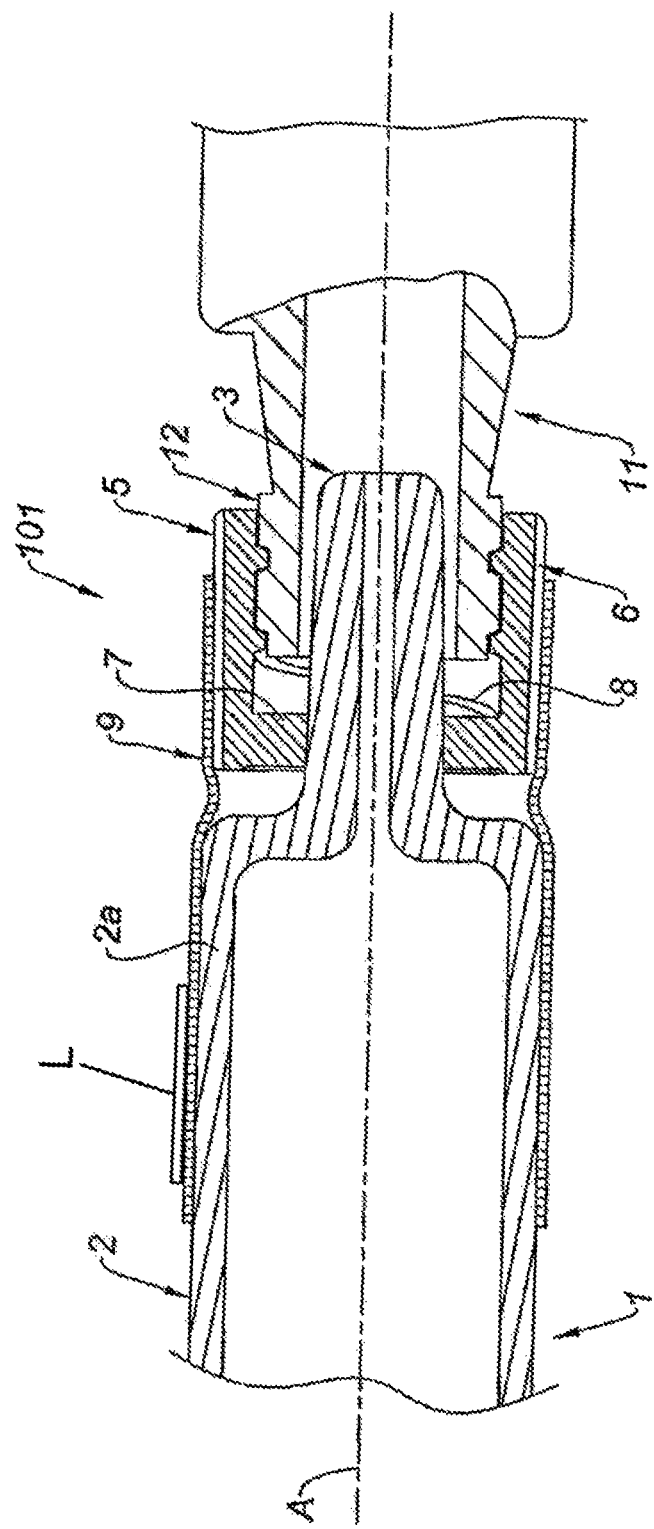

The invention and the advantages that arise therefrom will clearly emerge from the detailed description that is given below with reference to the appended drawings in which:

FIG. 1 is a perspective view of an injection device of the assembly of the invention together with an adaptor intended to be mounted on the distal tip of said device, FIG. 2 is a perspective view of the injection device and adaptor of FIG. 1 once the adaptor is mounted on the distal tip of said device, FIG. 3 is a partial cross section view of the assembly of the invention, FIG. 4 is a cross section view of the assembly of FIG. 3 wherein a plug has been mounted on the adaptor, FIG. 5 is a side view of an assembly in which the heat shrinkable film also covers part of a plug mounted on the adaptor, said heat-shrinkable film having a dot-line as tamper evident means, FIG. 6 is a cross section view of the assembly of FIG. 3 onto which a connector has been partly screwed.

DETAILED DESCRIPTION OF THE INVENTION

With reference to FIG. 1 is shown an injection device 1 of an assembly of the invention (shown on FIG. 3), comprising a container 2 comprising a distal tip 3 having a longitudinal axis A. As appears on this figure, the container 2 and the distal tip 3 are made of one single element. The container 2 has a tubular shape and defines a reservoir for a product, for example a medical fluid. The container 2 and the distal tip 3 are preferably made of glass material. The container 2 may be sealed at its proximal end by a piston (not shown). The distal tip 3 encompasses a channel 4 aligned with the longitudinal axis A and providing a passageway for the transfer of the product, either from the container 2 to a connector such as an IV connector, or from a vial to the container 2. On the example shown, the outer surface 3a of the distal tip 3 has a slightly tapered shape.

On FIG. 1 is also shown an adaptor 5 of the assembly of FIG. 3, said adaptor 5 comprising a ring 6. On the example shown the ring 6 is provided in its proximal region with an inner projection under the form of a discontinuous annular bulge 7 extending radially inwardly. The discontinuous annular bulge 7 is made of a material flexible enough to allow said discontinuous annular bulge 7 to expand slightly radially in the outward direction under pressure exerted on the inner wall of said bulge 7. Alternatively, the discontinuous annular bulge could be replaced by a continuous annular bulge capable of expanding radially outwardly. The inner wall of the ring 6 is provided with an internal thread 8 distally spaced from the discontinuous annular bulge 7. The adaptor 5 is preferably made of flexible material such as plastic.

As is shown on FIG. 2, the adaptor 5 is mounted on the distal tip 3 of the injection device 1. Thanks to the tapered shape of the outer surface 3a of the distal tip 3 and to the capability of the discontinuous annular bulge 7 to slightly expand radially outwardly, the adaptor 5 is mounted on the distal tip 3 by friction.

With reference to FIG. 3 is shown partially an assembly 101 of the invention in which the injection device 1 of FIG. 2 together with the adaptor 5 mounted on the distal tip 3, are further provided with a heat-shrinkable film 9 that has been bonded, for example by means of a glue, to part of the container 2 and part of the adaptor 5 and then heat shrunk so as to cover and wrap tightly at least part of said container 2, a distal region 2a of said container 2 on the example shown, and at least part of said adaptor 5, a proximal region 5a of the adaptor 5 on the example shown. The heat-shrinkable film 9 is continuous from the distal region 2a of the container 2 it covers until the proximal part 5a of the adaptor 5. For example, the heat-shrinkable film 9 may extend on said container 2 on a length equal or more than 5 mm and it may extend on said adaptor 5 on a length equal or more than 5 mm. The heat-shrinkable film 9 is made of a thermoplastic material. In an embodiment, the heat-shrinkable film 9 is made of polyvinyl chloride. In an embodiment the heat-shrinkable film 9 may be transparent and/or may comprise writing such as for example graduation, brand name.

In an embodiment of the invention not shown, the assembly 101 may further comprise a label imprisoned between the heat-shrinkable film 9 and the container 2 and adaptor 5. Alternatively, the label may be imprisoned between the heat-shrinkable film 9 and the container 2, or between the heat-shrinkable film 9 and the adaptor 5. In another embodiment of the invention not shown, the label may be located on the heat-shrinkable film 9, for example by gluing. Such a label may be a paper label and may be printed, for example with information relating to the contents of the container 2.

As appears from FIG. 3, thanks to the presence of the heat-shrinkable film 9, the adaptor 5 is prevented from rotating with respect to the container 2 and to the distal tip 3 around the longitudinal axis A. The heat-shrinkable film 9 therefore maintains the adaptor 5 blocked in rotation with respect to the container 2 around the longitudinal axis A. The heat-shrinkable film 9 also prevents the adaptor from translating with respect to the container 2.

As a consequence, when the user proceeds to the step of screwing a connector on the adaptor 5, the operation is facilitated and secure.

FIG. 4 shows the assembly 101 of FIG. 3 with a plug 10 mounted on the adaptor 5. This plug 10 is removably mounted on the adaptor 5 and is intended to close access to the adaptor 5 before use in order to protect said adaptor 5.

FIG. 6 shows the assembly of FIG. 3 during the step of screwing a connector 11 on the adaptor 5. Connector 11 is provided with an outer thread 12 intended to match the inner thread 8 of the ring 6 of the adaptor 5.

As a consequence, with reference to FIGS. 4 and 6, when the user, provided with an assembly 101 with a closed adaptor 5 as shown on FIG. 4, wishes to proceed to the further step of connecting to the adaptor 5 a connector 11, such as an IV connector, he first grasps the assembly 101 via the heat-shrunk film 9 in one hand and removes the plug 10. The user then just has to screw the connector 11 on to the internal thread 8 of the adaptor 5, as shown on FIG. 6, without bothering as to whether the adaptor 5 is immobile with respect to the distal tip 3 or not. Indeed, thanks to the film 9 heat-shrunk on the distal region 2a of the container 2 and on the adaptor 5 in a continuous way, the adaptor 5 is prevented from rotating and translating with respect to the distal tip 3, and therefore with respect to the container 2. When the external thread 12 of the connector 11 is firmly screwed on the internal thread 8 of the adaptor 5, then the user knows that the injection device 1 and the connector 11 are tightly connected without any risk of leakage of the product to be transferred from one piece to the other.

On FIG. 5 is shown an alternative embodiment of the embodiment of FIG. 4, in which the heat-shrinkable film 9 is longer and covers also part of the plug 10. The heat-shrinkable film 9 therefore covers part of the container 2, the adaptor (not shown on the FIG. 5 because entirely covered by the heat-shrinkable film 9) and part of the plug 10 in a continuous way. In such a case, for example, the heat-shrinkable film 9 is provided with an annular breakable line 13, like a dot-line or perforation line, which must be broken in order to remove the plug 10 and open the adaptor. The breakable line 13 therefore acts as a tamper evident means of the opening of the adaptor.

The assembly of the invention may be manufactured according to the following: an injection device comprising a container for a product, said container comprising a distal tip encompassing a channel providing a passageway for the transfer of said product, and a suitable adaptor are provided; by "suitable adaptor" is meant therein an adapting element having the adequate dimensions for being friction forced on the distal tip of the injection device. In a second step, the suitable adaptor is friction forced on the distal tip of said injection device. A heat-shrinkable film, for example made of polyvinyl chloride, under the form of a rectangular sheet, is bonded, for example by means of a glue, on the assembly so as to cover at least part of the adaptor and at least part of the container, preferably in a continuous way. In a further step, the heat-shrinkable film is heated until it shrinks and tightly covers said part of said container and said part of said adaptor, preferably in a continuous way. As a consequence, the heat-shrunk film maintains the adaptor blocked in rotation, around the longitudinal axis A, and in translation with respect to the container.

In the case where the heat-shrinkable film also covers part of a plug mounted the adaptor, the plug is mounted on the adaptor before bonding the heat-shrinkable film, and the length of the shrinkable film is chosen so as to cover entirely the adaptor and cover at least part of the plug, in particular in a continuous way. For example, a breakable line is designed in the area of the heat-shrinkable film intended to be bonded to the plug before said heat-shrinkable film is bonded to the container, the adaptor and the plug.

The assembly of the invention therefore allows connecting safely an injection device to a connector without having to check the tightness of the fixation between the injection device and the intermediate element formed of the adaptor.

The invention claimed is:

1. An assembly comprising:
    an injection device comprising a container for a product, said container comprising a distal tip encompassing a channel providing a passageway for transfer of said product;
    an adaptor comprising a ring mounted onto said distal tip, said ring including an internally threaded portion and an inner projection extending radially inwardly, wherein said ring of said adaptor is mounted on said distal tip by friction between said inner projection and said distal tip and wherein said distal tip extends into said internally threaded portion of said adaptor with a distal end of said distal tip being disposed beyond a distal end of said adaptor;
    a plug mounted on said adapter; and
    a heat-shrinkable film covering at least part of said container, said adaptor, and at least part of said plug, said heat-shrinkable film maintaining said adaptor blocked in rotation and in translation with respect to said container when said heat-shrunk film is in its heat-shrunk condition.

2. The assembly according to claim 1, wherein said inner projection is in the form of an annular bulge comprised of a flexible material.

3. The assembly according to claim 2, wherein said annular bulge is discontinuous.

4. The assembly according to claim 2, wherein said annular bulge is continuous.

5. The assembly according to claim 1, wherein said heat-shrinkable film is made of a thermoplastic material selected from the group consisting of polyvinyl chloride (PVC), a polyethylene terephthalate (PET), oriented polystyrene (OPS), oriented polypropylene (OPP), polylactic acid (PLA) and mixtures thereof.

6. The assembly according to claim 5, wherein said heat-shrinkable film is made of polyvinyl chloride.

7. The assembly according to claim 1, wherein said assembly further comprises a label imprisoned between said heat-shrinkable film and said container.

8. The assembly according to claim 1, wherein said assembly further comprises a label imprisoned between said heat-shrinkable film and said adaptor.

9. The assembly according to claim 1, wherein said assembly further comprises a label imprisoned between said heat-shrinkable film and said container and adaptor.

10. The assembly according to claim 1, wherein said assembly further comprises a label located on said heat-shrinkable film.

11. The assembly according to claim 1, wherein said heat-shrinkable film covers at least part of said container, said adaptor, and at least part of said plug in a continuous way.

12. The assembly according to claim 11, wherein said heat-shrinkable film is provided with an annular breakable line located on a part of the heat-shrinkable film that covers part of said plug.

13. The assembly according to claim 12, wherein said annular breakable line must be broken in order to remove said plug.

14. The assembly according to claim 1, wherein said heat-shrinkable film is at least partially glued on at least one of said container or adaptor.

15. The assembly according to claim 1, wherein said heat-shrinkable film is provided with writing.

16. The assembly according to claim 1, wherein said product comprises a medical fluid.

* * * * *